United States Patent [19]

Bogen et al.

[11] Patent Number: 4,877,035

[45] Date of Patent: Oct. 31, 1989

[54] MEASUREMENT OF THE END-SYSTOLIC PRESSURE-VOLUME RELATION USING INTRAAORTIC BALLOON OCCLUSION

[75] Inventors: Daniel Bogen, Philadelphia, Pa.; Krishanu Gupta, Cherry Hill, N.J.

[73] Assignee: Trustees of the University of Pennsylvania, Philadelphia, Pa.

[21] Appl. No.: 257,105

[22] Filed: Oct. 12, 1988

[51] Int. Cl.⁴ ................................................. A61B 5/02
[52] U.S. Cl. ..................................... 128/673; 128/344; 128/692; 128/694; 128/713
[58] Field of Search ................................ 128/672–675, 128/748, 668, 692, 694, 713, 341, 344

[56] References Cited

U.S. PATENT DOCUMENTS

| | | | |
|---|---|---|---|
| 4,051,841 | 10/1977 | Thoma | 128/672 |
| 4,592,364 | 6/1986 | Pinto | 128/672 |
| 4,621,646 | 11/1986 | Bryant | 128/692 |
| 4,664,125 | 5/1987 | Pinto | 128/672 |
| 4,733,652 | 3/1988 | Kantrowitz et al. | 128/672 |

Primary Examiner—Kyle L. Howell
Assistant Examiner—Angela D. Sykes
Attorney, Agent, or Firm—Woodcock Washburn Kurtz Mackiewicz & Norris

[57] ABSTRACT

Novel, noninvasive in vivo methods and apparatus for measuring the end-systolic pressure-volume relation and deriving peak end-systolic elastance, $E_{max}$, which do not alter intrinsic or reflex-stimulated cardiac contractility are disclosed. Afterload is varied by the controlled inflation of an intraaortic balloon catheter positioned in the ascending aorta. Balloon inflation is timed to transiently interrupt ventricular ejection at different times during the ejection phase, producing contraction at different ventricular volumes. Simultaneous measurements of left ventricular pressure and aortic volume during the occlusion sequence allows pressure vs. ejected volume loops to be generated, from which the slope of the end-systolic pressure-volume relationship, $E_{max}$ is determined.

$E_{max}$ was measured in 6 Dorsett sheep with normal, enhanced, and depressed contractile states. In the normal states, $E_{max}$ ranged from 1.01 to 5.08 mmHg/ml in animals with body weights ranging from 23 to 32 kg. This data was not significantly different ($p > 0.05$) from the $E_{max}$-body weight curve compiled from other measurements of $E_{max}$. After epinephrine infusion, $E_{max}$ increased from $3.07 \pm 1.49$ to $5.79 \pm 1.97$ mmHg/ml, consistent with previous investigations. Furthermore, serial measurements of $E_{max}$ tracked cardiac function even in severely depressed hearts or other biological pumps with rapidly changing contractility.

11 Claims, 5 Drawing Sheets

MEASUREMENT OF THE END-SYSTOLIC PRESSURE-VOLUME RELATION USING INTRAAORTIC BALLOON OCCLUSION

The present invention relates to methods and apparatus for determining the global ventricular contractility of a heart or other biological pump. The methods and apparatus disclosed measure and relate the ventricular pressure and ventricular volume under varied hemodynamic loading conditions to obtain data from which the end-systolic pressure-volume relation may be derived.

BACKGROUND OF THE INVENTION

Measurement of "ventricular contractility" has been an important but elusive goal, both in experimental cardiac mechanics and in the clinical assessment of patients with heart disease. This data is also useful for evaluating the performance and condition of any biological pump, such as a muscle pouch. The concept of the end-systolic pressure-volume relationship (ESPVR) has been developed and it is suggested that it could be used as an index of global ventricular contractility. See Monroe, R. G.; French, G. N., "Left Ventricular Pressure-Volume Relationships and Myocardial Oxygen Consumption in the Isolated Heart", Circ. Res. 9:362-374, 1961; Suga, H., et al.,"Controls of Ventricular Contractility Assessed by Pressure-Volume Ratio, $E_{max}$", Cardiovasc. Re. 10:582-592, 1976; Sagawa, K., "The Ventricular Pressure-Volume Diagram Revisited", Circ.Res. 43: 677-87 (No. 5, 1978); Sagawa, K., "Editorial: The End-systolic Pressure Volume Relation of the Ventricle: Definition Modifications and Clinical Use," Circulation 63: 1223-27 (No. 6,1981) all of which are incorporated herein by reference.

In principle, the measurement of ESPVR is straightforward: it requires only the acquisition of ventricular pressure-volume (PV) loops at two or more preload or afterload conditions. The end-systolic points on these PV loops are identified, and a line is drawn through them: the slope of this line is the end-systolic (peak) elastance, $E_{max}$. Previously, this procedure has been difficult to carry out, except in isolated-heart preparations. See Shroff, S.G. et al., "End-Systolic Relations: Their usefulness and Limitations in Assessing left Ventricular Contractile State", Int J. Cardiol. 5:253-259, 1984, which is incorporated herein by reference. Although intraventricular pressure is easily measured, typically with a catheter-tip manometer, both the determination of ventricular volume and the creation of altered afterload conditions have been problematic. It is for these reasons that the usefulness of the ESPVR measurement has not been fully evaluated, neither for experimental cardiac mechanics nor for clinical application.

Previous attempts to measure ESPVR, outside of the isolated heart preparation, have employed pharmacologic or mechanical vasodilator and constrictors to change afterload or preload. Grossman, W., et al., "Contractile State of the Left Ventricle in Man as Evaluated from End-Systolic Pressure-Volume Relation of Isolated Canine Heart", Circ. Res. 50: 727-734, 1982; Mehemel, H.C.,"The Linearity of the End-systolic Pressure-Volume Relationship in Man and Its Sensitivity for Assessment of Left Ventricular Function", Circulation 63: 1216-1222, 1981, both of which are incorporated herein by reference. Unfortunately, most of the interventions utilized in previous attempts act over extended periods of time and thus tend to stimulate physiologic feedback mechanisms which alter cardiac contractility. When blocking agents are used to counter these physiologic feedback mechanisms, there is a possibility of altering ventricular contractility by direct effects of the drugs. Even in the isolated heart preparation, where vascular, neural, and hormonal connections are severed to prevent reflex alterations in cardiac contractility, the isolated preparation develops changes in the basal contractility of the ventricle. In any case, up to the present time, a convenient method to alter afterload, *without altering ventricular contractility*, has been difficult to obtain.

In an attempt to overcome this problem, a servo-controlled syringe pump which is connected to the left ventricle through an apical cannula was devised. See Bogen, D. K., et al., "Measurement of Peak Systolic Elastance in Intact Canine Circulation with Servo Pump", Am. J. Physiol. 249:H585-593, 1985, which is incorporated herein by reference. When this device is operated in conjunction with an electropneumatic aortic occluder, afterload may be varied for the period of a single heartbeat or beat cycle of a biological pump, thus providing a range of loading conditions necessary to observe the ESPVR. This approach, however, is still limited. The instrumentation is complicated; repeated measurements of ESPVR in a chronic preparation would be difficult; and the clinical application of the servo-controlled syringe pump seems unlikely. Subsequently, a similar but simpler technique to measure ESPVR by occluding the aorta using Satinsky's vascular forceps was devised. However, this technique can only be utilized in acute studies and assumes that ESPVR is linear in all situations. However, this assumption is not necessarily correct; as of yet, linearity has not been shown in all pathologic states of the heart.

Therefore there exists a long-felt, but unsolved need for a useful technique to measure the ESPVR. This method must be simple, and allow serial determinations of the ESPVR in chronic preparations. Finally, this technique must be able to initiate transient variations in afterload and be easily adaptable for clinical measurement of the ESPVR.

OBJECTS OF THE INVENTION

It would be desirable to determine the end-systolic elastance of a heart or other biological pump, in vivo, under varying conditions of hemodynamic loading. Accordingly, it is an object of the present invention to provide methods and apparatus whereby the hemodynamic load placed upon the heart or biological pump may be varied, in vivo, in a controlled manner.

It would be further desirable to enable the obtainment of data which may be used to derive a value of the end-systolic elastance of a heart or biological pump. It is therefore an object of the present invention to provide methods and apparatus whereby ventricular pressure and volume data are obtained and a value of end-systolic elastance derived.

SUMMARY OF THE INVENTION

It has now been found that the controlled inflation of an intraaortic balloon can provide the necessary conditions which will allow data to be collected from which the end-systolic pressure volume relation and subsequently, $E_{max}$, may be derived.

According to the methods of the present invention, the end-systolic pressure volume relation and $E_{max}$ may be determined by obtaining data representative of ventricular pressure and volume, transiently altering the hemodynamic load of the heart or biological pump, and obtaining at least a second set of pressure and volume data. From the data collected, the end-systolic points of the heartbeats or beats of a biological pump may be identified, and $E_{max}$ derived by calculating the slope of a line passed through these points.

The present invention also discloses preferred apparatus, which permit controlled, transient intraaortic occlusion to be initiated. By using a novel intraaortic balloon, combined with a pneumatic system for inflation, the data required to calculate the end-systolic pressure-volume relation and $E_{max}$ may be collected. The pneumatic system disclosed is controlled by monitoring the ventricular pressure of the heart, and initiating occlusion at pre-determined values of ventricular pressure, most preferably a percentage of maximum ventricular pressure.

DETAILED DESCRIPTION

Using the methods and apparatus of the present invention ESPVR is determined from a series of ventricular PV loops obtained under varying afterload conditions. Intraventricular pressure is preferably measured by a catheter-tip manometer; ventricular volume is preferably measured by integrating the flow signal from an electromagnetic flow probe located at the aortic root. However, as explained below, other methods of determining ventricular volume are equally applicable to the present invention. In a most preferred embodiment, changes in afterload are produced by a novel method using the intermittent inflation of a small polyethylene balloon positioned in the ascending aorta. When the balloon is inflated for a single heat beat, the aorta is occluded, and ventricular ejection is interrupted. By timing the inflation of the balloon with respect to a cardiac cycle, it is possible to interrupt ejection at varying points within the ejection phase. This produces intervention beats in which systole commences normally, but terminates in isovolumic contraction at varying ventricular volumes. Since the occluding balloon is only inflated transiently, reflex changes in cardiac contractility are essentially eliminated.

Figure 1:
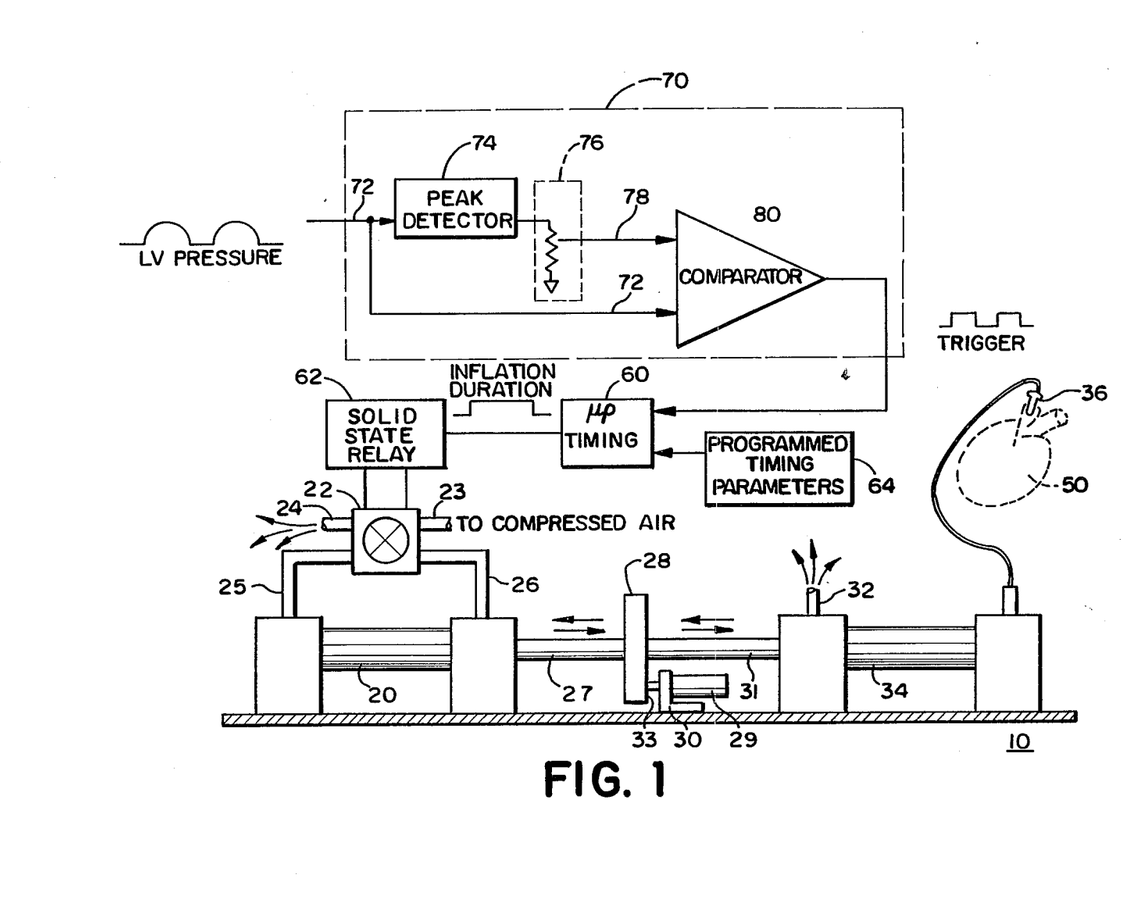
FIG. 1 is an elevation view depicting the intraaortic balloon catheter and the pneumatic system used to control its inflation; also depicted schematically is the circuitry used to control this apparatus.

Referring now to FIG. 1, the preferred apparatus used to carry out the methods of the present invention is illustrated. A pneumatically driven intraaortic balloon catheter system is shown generally as 10. The system is operated by a driving cylinder 20, the operation of which is regulated by a solenoid valve 22. The solenoid valve 22 regulates the intake by the driving cylinder 20 from a compressed air source 23, or allows compressed air to be exhausted via a suitable exhaust tube 24.

The motion of the driving cylinder 20 is controlled by a four-way solenoid valve 22, for example, Asco oodel 8342. There are two pneumatic ports 25,26 which enter the driving cylinder chamber on either side of the piston. One of these ports is always connected to the source of compressed air or other gas 23; the other 24, serves as an exhaust port to the atmosphere. The four-way valve 22 switches the compressed air from one side of the piston 20 to the other, causing the actuator rod 27 to move outward (balloon inflation) or inward (balloon deflation).

The inflation volume of the intraaortic balloon 36 is adjusted by setting the distance that the actuator rods 27,31 travel. This is accomplished by adjustable mechanical stops 28,30 which limit the motion of the actuator rods. The mechanical stops have both coarse and fine adjustments. The coarse adjustment is governed by positioning a first stop 28 on the compressor-side actuator rod 27. In a preferred embodiment, the stop 28 is an aluminum disc of sufficient diameter to come into contact with the fine adjustment stop 30. The fine adjustment stop 30 makes use of a micrometer head 29 to allow for precise regulation of cylinder travel.

The pressure of the compressed air source is regulated by a 0–100 psi regulator 19, not illustrated. In operation, the pressure is set so that the balloon 36 can be inflated within a specified time period. Time for inflation is measured by using an electrical switch 33 to detect the contact of the actuator rod 27 against the mechanical stop 28. The time between the turn-on signal to the solenoid 22 to the actuator stop signal may be measured with a digital storage oscilloscope, not illustrated. A regulated pressure of 30 psi is preferably used, and produces balloon inflations within 26.7±4.1 msec. The inflation time of the balloon 36 is actually somewhat less than this, since the measured time includes the delay in solenoid activation.

Figure 7:
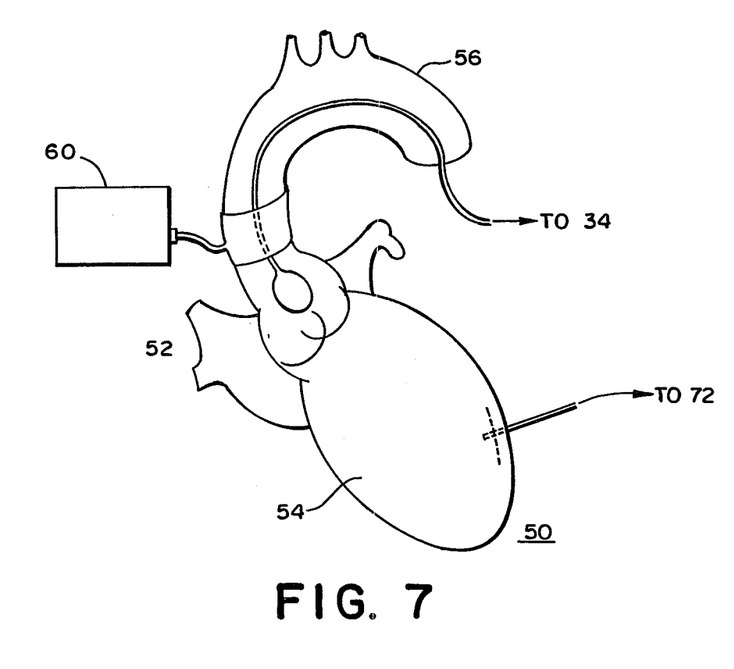
FIG. 7 is a partial pictorial representation of the preferred apparatus of the present invention and its placement within a portion of a heart.

As shown in FIG. 7, the aortic occluding balloon 36 is a 5 cc polyethylene balloon, with 22mm (inflated) outer diameter, attached to a 8.5 Fr. catheter. This was custom-designed and fabricated by DataScope (Oakland, NJ). The balloon catheter 36 is preferably inserted into the heart 50 and is most preferably positioned approximately 1-2 cm distal to the aortic valve 52 in the aortic root, but proximal to the innominate takeoff. Those of ordinary skill will realize that other placements or placements within other biological pumps are possible and useful in practicing the present invention. FIG. 7 also illustrates those portions of the heart 50 necessary to illustrate the placement of the apparatus of the present invention. Shown are the aortic valve 52, the left ventricle 54, and the aorta 56.

Also illustrated in FIG. 7 is the placement of the electromagnetic flow cuff 60, which is preferably used to gather data from which ventricular volume may be derived. Those of ordinary skill will realize that in clinical or other applications, other methods of estimated or measuring ventricular volume may be employed. For example, in a clinical situation, non-surgical methods of measuring volume, such as radiographic imaging, volume conductance catheters, or flow catheters will preferably be employed.

The positioning of a micromanometer 65 used to generate a signal 72 representative of left ventricular pressure is also seen in FIG. 7. As with the measurement of volume, it will be appreciated that alternative positions and embodiments of pressure measuring apparatus may be employed in order to practice the present invention.

A commercial embodiment of the present invention may combine an annular balloon catheter 36, having volume and pressure measuring apparatus 60,65 integrated into the center of the annulus. The resulting device would essentially be a three channel catheter which would provide the data necessary to determine the ESPVR with a single insertion.

The occluding balloon 36 is inflated pneumatically by an electropneumatic actuator 34. The balloon catheter is connected to the output port of a small bore (1.91 cm) air cylinder 34, such as Aurora Air Products style B-12. When the piston of this air cylinder 34, termed the "inflation cylinder", is pushed by actuator rod 31 inward, air is displaced into the balloon. The motion of the actuator rod 31, in turn, is generated by directing compressed air into the driving cylinder 20 described above. This causes the piston of the driving cylinder 20 to be displaced outward. Since the actuator rods 27,31 of the two air cylinders are connected in series, compressed air applied to the driving cylinder 20 causes air to be displaced out of the inflation cylinder 34 and into the balloon 36. For these air cylinders 20, 34, the actuator rod stroke is 11.43 cm, which corresponds to a maximum possible air displacement into the balloon of 32.55 cc.

A microprocessor based timing system 60 allows the balloon 36 to be inflated at designated times within a cardiac cycle. This can be accomplished, for example, by monitoring the electrical impulses which regulate cardiac activity, for example, by using the signals generated by an electrocardiogram (EKG). However, since the coupling between EKG signals and mechanical contraction is not constant, particularly in pathologic states, the preferred embodiment of the control system of the present invention uses, instead, a ventricular pressure signal to establish the timing reference. Essentially, an analog circuit 70 follows left ventricular pressure, and recognizes when ventricular pressure reaches a set fraction of peak pressure. This function is shown schematically in FIG. 1. The ventricular pressure signal 72 goes to a peak detector 74 whose output passes to an adjustable voltage divider 76; the output, or threshold signal 78, is thus a percentage of peak ventricular pressure. The peak detector circuit 70 has a time constant of 1 sec to filter out sudden fluctuations in peak ventricular pressure. The ventricular pressure signal 72 is then compared with the threshold signal 78 by an analog comparator circuit 80. When the rising ventricular pressure reaches the threshold value, the output of the comparator 80 undergoes a step change which is tied to the input port on a microprocessor controller 60. The controller 60 senses this event within the cardiac cycle and initiates balloon inflation after a programmable time delay. The microprocessor timing system 60 is preferably a FORTH-based microcomputer board. In a most preferred embodiment a New Micros board with a Rockwell R6512 microprocessor is used. The microprocessor controller 60 also preferably includes internal counter/timer circuitry and multiple I/O ports. It will be understood by those of ordinary skill that the time delay software, is thus written in FORTH and assembly language, and is permanently stored in EEPROM.

EXAMPLE I

The microprocessor based timing system 60 also has the capability to receive programming inputs related to timing parameters, as shown functionally at 64. For example, in a preferred embodiment, the timing system is programmed to produce an alternating sequence of balloon occlusions and control periods. Most preferably, the sequence is comprised of three single beat occlusions, with intervening control periods of non-occluded beats.

The intraaortic balloon occluder of the present invention was tested in six Dorsett sheep with normal, enhanced, and depressed contractile states. End-systolic elastance, $E_{max}$ was measured in each case and compared with measurements of $E_{max}$ obtained by other techniques.

Six healthy Dorsett sheep (average weight 26±2.4 kg) were studied. Anesthesia was induced with sodium pentothal (25mg/kg) and was maintained with halothane (0.5–1.0%) after endotracheal intubation and mechanical ventilation (Harvard model 607, tidal volume 12–18cc/kg.). Atropine, 1 mg. I.V., was given Q 1 hr. to control ovine bronchial secretions. D5NS was infused at 5cc/kg/hr plus replacement volume. Packed red blood cells (PRBC) were transfused to keep hematocrit greater than 25.

A median sternotomy was performed and the chest opened with the heart suspended in a pericardial cradle. Additional incisions were made in the neck to expose the external jugular vein and the internal carotid artery for placement of the Swan Ganz catheter and the aortic occluder balloon, respectively. The vagus nerve was left intact bilaterally. A groin incision was also made to expose the femoral artery for subsequent cannulation.

Left ventricular cavitary pressure was monitored with a 5F micromanometer-tipped catheter (Millar Instruments, SPC-350) introduced through the left ventricular free wall. The transducer was interfaced with a Millar (TCB-500) control unit. To measure aortic flow, an electromagnetic flow probe (Biotronix BL-5000) was placed around the root of the aorta distal to the coronary ostia, but proximal to the origin of the innominate takeoff. The probe was operated with a Biotronex pulsed-logic blood flowmeter (BL-610). A 7F Swan-Ganz catheter was placed in the pulmonary artery and used to measure core temperature and thermodilution cardiac output (Gould SP1435). Body temperature was maintained between 36.5° C. to 39° C., and the electrocardiogram was continuously monitored using a Gould (ES-1000B)ECG amplifier.

For each sheep, (n=6), end-systolic elastance was measured with the balloon occluder under three conditions associated with different contractile states: control (normal contractility), epinephrine administration (enhanced contractility), and global ischemia (depressed contractility). After each sheep was fully instrumented, occluder triggering and timing parameters were set. First, the trigger threshold (fraction of peak systolic pressure) was set to a point just before ventricular ejection occurred, at roughly 50% of peak systolic pressure. Second, the timing system was programmed to produce an alternating sequence of balloon occlusions and control periods. The sequence consisted of three single-beat occlusions, with intervening control periods of four non-occluded beats. The occlusions were timed so that they occurred just prior to ejection, at peak systolic pressure, and during the late ejection period. These timings are heart-rate dependent; but for an average heart rate of 100 bpm, the occlusions were typically 0, 80, and 125 msec after the trigger point. Inflation duration was set to extend through the early diastolic phase of the following beat; this period was typically 300 msec.

With these settings, with the heart in the control state, pressure-flow data was recorded during the occlusion sequence described above. For each data acquisition run, an additional 10 seconds of data was recorded both before and after the occlusion sequence. If, during data acquisition, a premature contraction occurred, or the occluder timing was not properly set (e.g. because of a change in heart rate), that data was rejected for subsequent analysis and additional runs were made. A minimum of five acceptable data runs were obtained for each sheep in the normal state.

A state of enhanced contractility was obtained by administering a continuous epinephrine drip at 0.5 g/Kg/min. After 15 minutes, balloon occlusion measurements of end-systolic elastance were obtained using the same protocol employed for the normal heart. Since epinephrine increased the heart rate, the inflation times (delay from threshold trigger and inflation duration) were shortened.

A state of depressed contractility was obtained by 15 minutes of warm global ischemia. First, the animal was placed on full cardiopulmonary bypass (CPB). The CPB system consisted of a blood reservoir, an extracorporeal flow probe (Biotronix, BLX-2096), a combined heat exchanger/hollow fiber membrane oxygenator (0.8M2, Maxima-Johnson & Johnson) and a centrifugal blood pump (Biomedicus 520-C). The CPB circuit was primed with 500cc of saline and 1000cc hetastarch (DuPont). The animal was heparinized (15,000 units load then 10,000 units Qlh), and the CPB circuit was completed by placing a 32F venous cannula (Sarns) in the right atrium and a 14F arterial catheter (USCI) into the femoral artery. The aorta was cross-clamped for 15 minutes and the heart was allowed to fibrillate. The left ventricle was vented only during the ischemic period.

After the cross-clamp was removed, the heart was reperfused on full CPB for a minimum of 20 minutes. The reperfusion period was variable as each individual sheep required different levels of post-ischemic resuscitation before it could be weaned off CPB. Resuscitation included small doses of epinephrine (0.2 mg/hr), lidocaine (50mg bolus followed by a 1 mg/min drip), sodium bicarbonate (½ ampule) and, if necessary, defibrillation.

When the animals could be weaned off of CPB, measurements of end-systolic elastance were obtained using the same basic protocol employed for the normal heart. Because of the hemodynamic instability of the globally ischemic ventricle, occluder timing had to be continually readjusted to follow the changing state. Timing was reset by performing 1-2 preliminary data runs to confirm that aortic occlusion occurred at the desired points within the cardiac cycle.

At the conclusion of the protocol, the animals were sacrificed. The hearts were excised; the right ventricular free wall, fat, and valvular tissue were dissected away from the left free wall and the septum, and the remaining left ventricle was weighed. In addition, the ascending aorta, with flow cuff still attached, was removed to calibrate the electromagnetic aortic flow pump, and the flow probe value was calibrated against the extracorporeal flow meter.

For each data run, left ventricular pressure, aortic flow, ECG, and occluding balloon timing signals were simultaneously recorded on a 16 channel electrostatic chart recorder, such as a Gould ES 1000 and digitally sampled by a 16 channel 12 bit analog-to-digital converter board, such as a Tecmar Lab Master in a Sperry IT personal computer. All signals were sampled at 100 Hz and later digitally filtered with a 50-Hz low-pass filter.

Data analysis preferably consists of (1) constructing pressure-volume (PV) loops for normal and occluded beats; and (2) computing the end-systolic pressure-volume relationship (ESPVR). The PV loops use ventricular volume expressed as the volume ejected from the ventricle during the systole. Ejected volume is obtained by digitally integrating the aortic flow signal over the period of a single beat, from end-diastole to end-diastole, although in alternative embodiments direct measurement of ventricular volume can be utilized. End-diastole is defined as occurring when dP/dt, the rate of the pressure rise, reaches 25% of the maximum value. During some balloon occlusions, a large negative flow signal was recorded from the electronic flow meter. This may be the result of the close proximity between the balloon and the flow cuff. Accordingly, the flow signal was digitally clipped to eliminate negative values.

The end-systolic elastance may be computed from a number of occlusion loops along with one non-occlusion loop. In the present Example, three occlusion loops are used. End-systolic elastance, $E_{max}$, and unstressed volume, $V_o$, are determined so as to satisfy the equation:

$$P_{es} = E_{max}(V_{es} - V_o) \quad (1)$$

where $P_{es}$ and $V_{es}$ are the end systolic pressure and volume, respectively.

To find $E_{max}$ and $V_o$ a numerical scheme is employed. First, an initial estimate for $V_o$ is made. Then, for each PV loop, the instantaneous elastance, E(t), is calculated using the equation:

$$E(t) = P(t)/[V(t) - V_o] \quad (2)$$

For each loop the P(t) and V(t) associated with the maximum value of E(t) is identified. A linear regression of these PV points is carried out. The volume intercept, the point at which the regression line crosses the volume axis, is taken as the new estimate for $V_o$. The steps of this method are repeated until $V_o$ converges. The final regression line is the ESPVR, with the volume intercept being $V_o$ and the slope being $E_{max}$ in equation (1).

Figure 2A:
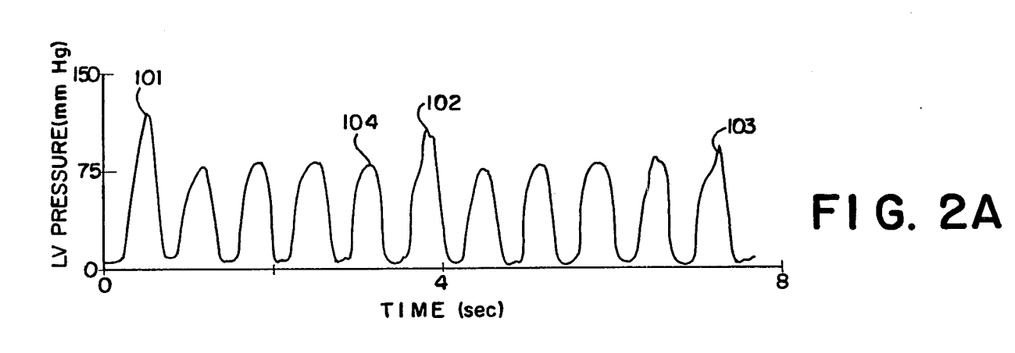
FIG. 2 depicts typical pressure and flow data collected using the methods and apparatus of the present invention.
Figure 2B:
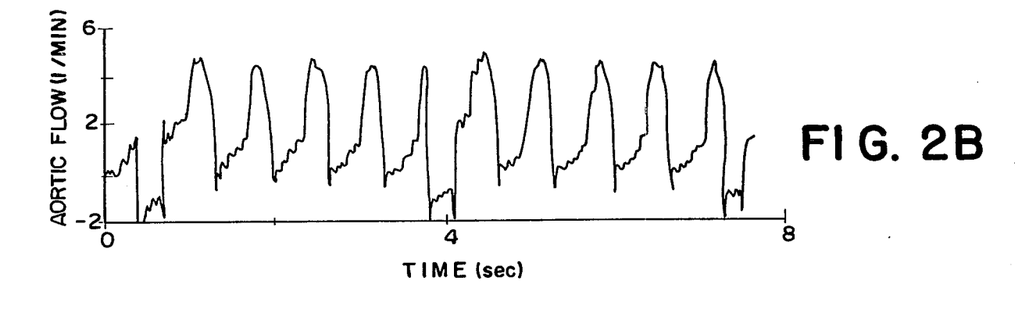

The operation of the balloon occluder system can be further understood by referring to FIG. 2. Shown in FIG. 2 are left ventricular pressure (FIG. 2A) and aortic flow (FIG. 2B) traces in which four different afterload conditions are observed in a normal sheep heart. Four heart beats are lablled in FIGS. 2A and 2B as 101, 102, 103 and 104. The first three heartbeats 101, 102, 103 correspond to one of the balloon occlusions and the fourth 104 to a nonoccluded beat. A first beat 101 is a nearly isovolumic beat, where the occlusion occurred slightly after ventricular ejection began. In a second beat 102, occlusion occurred at a point which would ordinarily fall in the mid-ejection period. For a third beat 103, occlusion occurred late in the systole. Therefore, for the case of early occlusion 101, there is very little aortic flow and a substantial increase in peak systolic pressure. In the case where occlusion occurred in the middle of the cycle, 102 aorticflow is reduced in both duration and amplitude, with an integrated flow (ejection volume) about one-half of normal. For this beat 102, there was also an increase in peak ventricular pressure. Finally, the case of late occlusion 103 aortic flow and peak systolic flow is slightly increased above normal. The normal beat 104, is taken as a fourth afterload condition.

Figure 3:
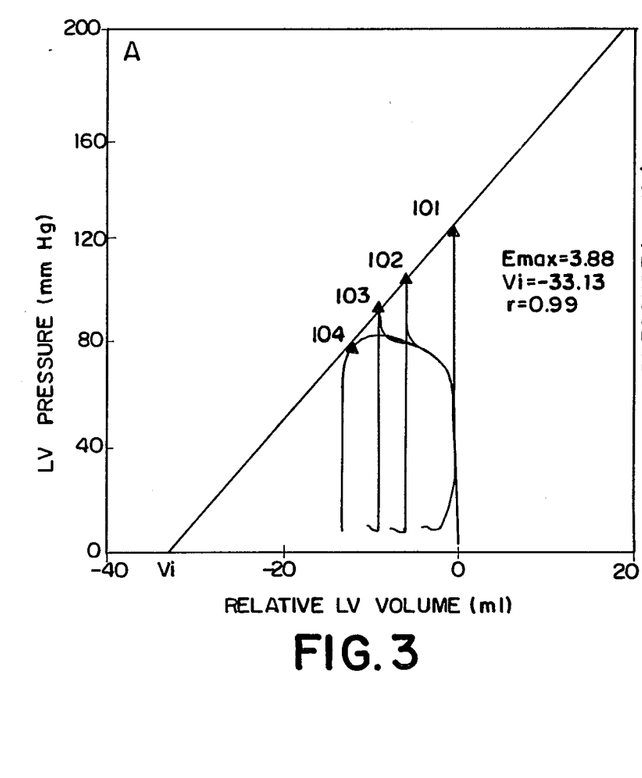
FIG. 3-5 are rectilinear plots of end-systolic values of pressure and volume derived from the data collected using the present invention.

Referring now to FIG. 3, there is illustrated the pressure-volume loops computed from the pressure-flow traces illustrated in FIG. 2. The reference numerals 101, 102, 103 and 104 correspond to those heartbeats identified in FIG. 2, the end-systolic points are identified by solid triangles. The volume measure, relative LV volume, is defined as the negative integrated aortic flow, one of ordinary skill will understand that other methods of measuring volume are also applicable to the present invention. Thus, end-diastolic volume is associated with a relative volume of zero. The PV loops for the occluded beats 101, 102, 103 initially follow the loop for the unoccluded beat 104, but make a sharp transitions isovolumic systole as the aorta becomes occluded by the balloon. The end-systolic pressure-volume relation, given by the straight line in FIG. 3, was calculated by the iterative method described above. The four end-systolic points fit the line quite closely, with a correlation coefficient of 0.99. The slope of this curve, or peak elastance, is 3.88 mmHg/ml; and the volume intercept, $V_i$, is $-33.13$ ml.

To verify that the operation of the occluder did not affect the baseline contractility of the ventricle, a comparison was made between pre- and post-occlusion beats. Pressure and flow data from the five beats immediately preceding the occlusion sequence were averaged together; pressure and flow data from the five beats immediately following the sequence were similarly averaged. Comparisons were made for $P_{max}$, stroke volume, and the area under the pressure-volume loop for 6 normal sheep hearts. The range of variations were 0.48–1.98% for $P_{max}$, 0.91–11.61% for stroke volume, and 2.61–9.14% for PV area.

EXAMPLE II

Six healthy sheep, with body weights ranging from 23-32 kg (mean 26.8±3.1 kg), were studied according to the protocol previously described. Hemodynamic parameters and end-systolic elastance, $E_{max}$, were measured under normal and epinephrine-enhanced contractility. The parameters are summarized in Table I. As is usual with epinephrine administration, the heart rate, peak left ventricular pressure (LVP), maximum dP/dt, cardiac output, and stroke volume all increased. With epinephrine infusion, heart rate increased, on average, from 108.05 to 135.07 bpm. In spite of shortened systolic period with these faster heart rates, the balloon occluder system continues to function without any difficulty. Stroke volume increased from 19.25 to 25.25 ml; this improves volume measurements since the signal-to-noise ratio of the aortic flow is increased. Similarly, the peak LVP increased from 93.82 to 111.70 mmHg. Added to Table I are the body weights and LV weights for each of the experimental animals.

Figure 4:
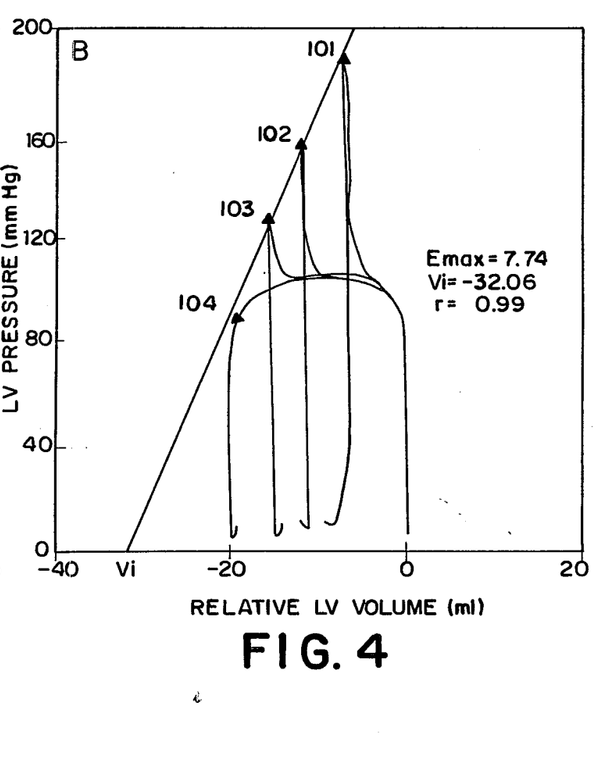

Pressure-volume loops for a typical experiment with enhanced contractility are shown in FIG. 4. This is the same heart as shown in FIG. 3. Four different afterload conditions are shown as before. The end-systolic points are virtually collinear (correlation coefficient=0.99). The end-systolic elastance for this example is 7.74 mmHg/ml, compared to 3.88 mmHg/ml for the normal contractile state, nearly a two-fold increase in contractility.

Table II summarizes the measurement of the end-systolic pressure-volume relationship. For each animal, $E_{max}$ is given for both contractile states, along with the volume intercept, $V_i$, and statistical information. Contractile states are compared using two types of regression analyses to calculate ESPVR. In the first, under the heading "Mean" in Table II, $E_{max}$, $V_i$, and the correlation coefficient were computed for each occlusion sequence and the results averaged together. The standard deviation for $E_{max}$, therefore, describes the reproducibility of the elastance measurement. Standard deviations were in the range of 0.14 to 0.72 mmHg/ml in the normal heart, indicating that at a given contractile state the measurement is very repeatable.

The second regression method, under the heading "Pooled" in Table II, takes the entire set of end-systolic points from all occlusion sequences associated with a given contractile state and animal, and computes $E_{max}$, correlation coefficient, and $V_i$ for the pooled data.

Statistical comparisons were performed on both mean and pooled $E_{max}$, and $V_i$. Each of the distributions were first found to be normal using the Wilk-Shapiro test for normality. Then a two-tailed paired t-test was employed to compare the enhanced state with the normal state. The mean peak elastance, $E_{max}$, was significantly different (p=0.004); while the pooled $E_{max}$, also significantly different, had a lower p-value (0.039). There was no statistically significant change in $V_i$ between the two contractile states in either mean or pooled cases.

EXAMPLE III

Figure 5:
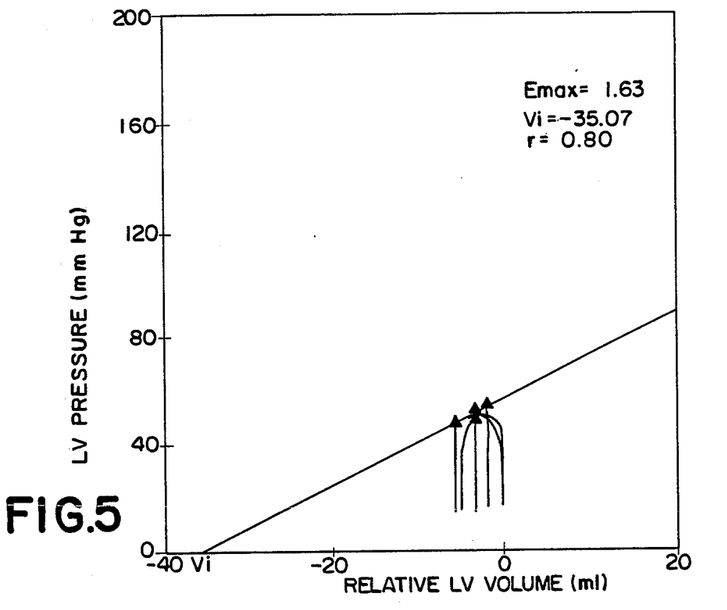

All of the animals studied under normal and enhanced contractile states were subjected to global ischemia, as described above and studied with the aortic balloon occluder. Although the apparatus continued to function for severely depressed ventricles, it was not always possible to determine an ESPVR. In some cases, ventricular ejection was so limited that partial aortic occlusion, in absolute terms, was only marginally reduced. In other cases, although larger changes in ventricular ejection could be produced, only negligible changes in peak ventricular pressure were observed. Even under the best circumstances the range of end-systolic pressure-volume points was small, as shown in FIG. 5. This reduced the quality of the linear regression to the end-systolic points.

Figure 6:
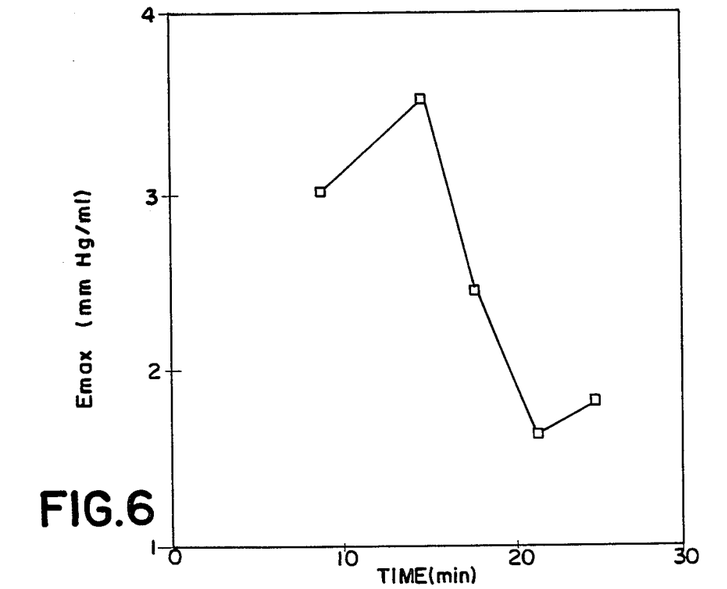
FIG. 6 shows the rapid deterioration of $E_{max}$ in a globally ischemic heart.

FIG. 5 shows results obtained from one sheep approximately 21 minutes after cardio-pulmonary bypass was removed, and epinephrine infusion was stopped. Here, $E_{max}$ was 1.63 mmHg/ml, compared to 2.56 mmHG/ml in the normal state. This measurement was one of a series of measurements taken after mechanical and pharmacological support of the heart were removed. The entire series is summarized in FIG. 6, which shows $E_{max}$ over a 25 minute time period. The rapid deterioration in contractility is apparent, and it indicates the difficulty in assigning one particular value to $E_{max}$ in these severely depressed ventricles. However, this data demonstrates that the balloon occluder measurement technique can be used to follow the time course in $E_{max}$ even when contractile state is changing quickly.

One of ordinary skill in the art will appreciate, that although particular embodiments of apparatus and certain method steps have been described in detail, variations employing the spirit of the present invention are possible. The full scope of the present invention may be determined by reference to one or more of the appended claims.

TABLE I

| | | | | Hemodynamic Effects of Enhanced Inotropism | | | | |
|---|---|---|---|---|---|---|---|---|
| Sheep No. | Body Wt. | LV Wt. | Inotr. State | HR | SV | CO | Peak LVP | Max dP/dt |
| EDAT14 | 23 | 70 | N | 91.93 ± 2.41 | 12.71 ± 1.12 | 1.68 ± 0.07 | 88.17 ± 6.44 | 689.11 ± 88.39 |
| | | | E | 126.43 ± 3.98 | 20.10 ± 1.72 | 3.87 ± 0.44 | 103.12 ± 5.80 | 1736.99 ± 199.99 |
| EDAT15 | 28 | 76.5 | N | 102.40 ± 1.21 | 23.98 ± 2.45 | 3.29 ± 0.15 | 112.70 ± 2.95 | 1361.09 ± 34.79 |
| | | | E | 144.16 ± 1.80 | 17.79 ± 2.28 | 4.26 ± 0.31 | 121.67 ± 7.95 | 2616.39 ± 214.71 |
| EDAT16 | 27 | 75.1 | N | 119.14 ± 4.12 | 12.66 ± 0.56 | 2.40 ± 0.14 | 93.44 ± 7.27 | 893.55 ± 27.32 |
| | | | E | 119.10 ± 2.53 | 14.93 ± 0.52 | 3.77 ± 0.35 | 106.25 ± 4.43 | 1733.44 ± 108.91 |
| EDAT17 | 24 | 62 | N | 121.47 ± 1.27 | 18.65 ± 0.85 | 2.23 ± 0.19 | 107.23 ± 0.65 | 1197.84 ± 14.99 |
| | | | E | 144.13 ± 4.49 | 28.92 ± 3.37 | 4.07 ± 0.48 | 118.26 ± 10.87 | 2378.20 ± 462.24 |
| EDAT18 | 32 | 92 | N | 104.78 ± 4.62 | 23.39 ± 2.40 | 1.98 ± 0.17 | 86.52 ± 3.27 | 649.98 ± 32.22 |
| | | | E | 125.51 ± 1.43 | 43.26 ± 4.20 | 4.24 ± 0.20 | 111.58 ± 5.82 | 1909.52 ± 102.10 |
| EDAT19 | 27 | 69 | N | 108.55 ± 2.49 | 24.10 ± 0.59 | 2.81 ± 0.20 | 74.83 ± 2.34 | 893.65 ± 41.44 |
| | | | E | 150.83 ± 3.45 | 26.49 ± 0.91 | 5.13 ± 0.77 | 109.34 ± 3.54 | 2452.06 ± 127.55 |
| Mean | 26.8 ± 3.1 | 74.1 ± 10.2 | N | 108.05 ± 11.01 | 19.25 ± 5.47 | 2.40 ± 0.58 | 93.82 ± 14.02 | 947.54 ± 281.01 |
| | | | E | 135.07 ± 12.92 | 25.25 ± 10.28 | 4.22 ± 0.49 | 111.70 ± 7.09 | 2137.77 ± 390.35 |

Animal body weight is in kg; left ventricular weight in gm. The hemodynamic parameters and means are expressed as Mean ± SD; N, normal inotropic state, E, enhanced state using 0.5 μg/Kg/min of epinephrine; HR. heart rate in beats/min; SV, stroke volume in ml, calculated from the integration of aortic flow; CO, cardiac output in l/min. measured by thermodilution; LVP, left ventricular pressure in mmHg; dP/dt, first derivative of LVP in mmHg/sec.

TABLE II

| | | | Influence of Enhanced Inotropism on $E_{max}$ and $V_1$ | | | | | |
|---|---|---|---|---|---|---|---|---|
| Sheep No. | Inotr. State | # Occl. Runs | Mean | | | Pooled | | |
| | | | $E_{max}$ | $V_1$ | r | $E_{max}$ | $V_1$ | r |
| EDAT14 | N | 8 | 4.19 ± .47 | −33.59 ± 4.15 | .99 | 3.90 | −35.07 | .90 |
| | E | 4 | 8.73 ± .78 | −28.71 ± 3.28 | .99 | 7.33 | −31.52 | .83 |
| EDAT15 | N | 5 | 2.56 ± .29 | −67.65 ± 6.96 | .84 | 2.55 | −67.19 | .83 |
| | E | 4 | 6.24 ± 1.31 | −31.98 ± 6.32 | .92 | 4.09 | −42.07 | .73 |
| EDAT16 | N | 6 | 5.08 ± .72 | −28.49 ± 3.87 | .98 | 5.25 | −27.29 | .96 |
| | E | 5 | 6.81 ± .44 | −27.28 ± 1.76 | .93 | 6.62 | −27.71 | .91 |
| EDAT17 | N | 5 | 3.54 ± .14 | −48.36 ± 1.49 | .99 | 3.65 | −47.47 | .98 |
| | E | 6 | 4.54 ± .55 | −50.77 ± 7.44 | .99 | 2.81 | −69.16 | .68 |
| EDAT18 | N | 7 | 1.01 ± .25 | −106.43 ± 28.97 | .88 | 0.94 | −108.69 | .75 |
| | E | 8 | 2.98 ± .62 | −64.53 ± 10.47 | .98 | 2.69 | −68.02 | .94 |
| EDAT19 | N | 5 | 2.01 ± .26 | −57.17 ± 6.09 | .98 | 1.97 | −57.94 | .94 |
| | E | 5 | 5.45 ± .43 | −40.97 ± 1.06 | .99 | 5.30 | −41.60 | .98 |
| p values* | | | .004 | NS | | .039 | NS | |

The inotropic states are, N, normal, and, E, enhanced with a 0.5 μg/Kg/min epinephrine drip. Number of occlusion runs represent the number of individual occlusion sequences. Mean ± SD values are the averages of regressions on each of the individual occlusion sequences; the pooled data are obtained when a linear fit is performed on the combined end-systolic points from all occlusions associated with a given contractile state and animal. $E_{max}$ is the peak elastance; $V_1$, the volume intercept, and r, the corrolation coefficient.
*Two-tailed paired t-test of normal vs enhanced states; NS, not significant at $p > 0.05$.

What is claimed is:

1. A method of determining an index of the global ventricular contractility of a biological pump, comprising the steps of:
   (a) acquiring data representative of ventricular pressure and data representative of ventricular volume of the biological pump during at least one beat of the biological pump;
   (b) transiently altering the hemodynamic load of the biological pump;
   (c) acquiring data representative of ventricular pressure and data representative of ventricular volume of the biological pump during at least one beat of the biological pump while the biological pump is in the altered hemodynamic state;
   (d) identifying the pressure and volume data value associated with the end-systolic point of the beats the biological pump of steps (a) and (c); and (e) relating the data identified in step (d) to the end-systolic elastance of the biological pump.

2. The method of claim 1, wherein said transiently altered hydrodynamic load is initiated by a variable afterload.

3. The method of claim 2, wherein said varying afterload is produced by intermittent blockage of the aorta.

4. The method of claim 3, wherein said intermittent blockage of the aorta is produced by the inflation of an intraaortic balloon catheter 5. The method of claim 4, wherein said inflation of an intraaortic balloon catheter is timed to transiently interrupt ventricular ejection at different times during the ejection phase, to produce isovolumic contraction at differing ventricular volumes.

6. The method of claim 1, wherein steps (b) and (c) are repeated to acquire a plurality of data sets, each associated with a different altered hemodynamic load.

7. The method of claim 1, wherein step (e) is further comprised of:
   performing a linear regression to determine the slope of a line connecting the end-systolic pressure and volume data pairs identified in step (d).

8. Apparatus for determining an index of global ventricular contractility of a biological pump, comprising:
   (a) means for transiently and intermittently occluding the aorta of a biological pump;
   (b) means for acquiring data representative of ventricular pressure of the biological pump;

(c) means for acquiring data representative of ventricular volume of the biological pump;

(d) means for monitoring the data representative of ventricular pressure and determining if said ventricular pressure has reached a specified value;

(e) means for transmitting a control signal, said control signal being transmitted upon said ventricular pressure reaching said specified value; and (f) means for actuating said means for occluding an aorta, said actuation means governed by said control signal.

9. The apparatus of claim 8, wherein said means for transiently and intermittently occluding the aorta of a biological pump is comprised of:
  (a) intraaortic balloon catheter;
  (b) means for inflating said balloon catheter;
  (c) means for controlling the amount of inflation of said balloon catheter and
  (d) means for inflating said balloon catheter at designated times within a cardiac cycle.

10. The apparatus of claim 8, wherein said means for determining ventricular pressure is a catheter-tip manometer.

11. The apparatus of claim 8, wherein said means for determining aortic volume is an electromagnetic flow probe.

* * * * *

UNITED STATES PATENT AND TRADEMARK OFFICE
CERTIFICATE OF CORRECTION

PATENT NO. : 4,877,035

DATED : October 31, 1989

INVENTOR(S) : Daniel Bogen; Krishanu Gupta

It is certified that error appears in the above-identified patent and that said Letters Patent is hereby corrected as shown below:

Col. 1, line 5,
After the title, before the first paragraph, insert a new paragraph as follows:

--The invention disclosed herein was supported in part by Grant No. R01-HL-36308; the U.S. Government may have certain rights in this invention.--

Col. 4, line 5, change "oodel" to --Model--.

Col. 8, line 59, change "lablled" to --labelled--.

Col. 9, line 3, change "aorticflow" to --aortic flow--.

Signed and Sealed this

Twenty-fifth Day of April, 1995

Attest:

BRUCE LEHMAN

Attesting Officer

Commissioner of Patents and Trademarks